United States Patent
Buchi et al.

(10) Patent No.: US 10,155,719 B2
(45) Date of Patent: Dec. 18, 2018

(54) METHOD OF PURIFYING NITRATED AROMATIC COMPOUNDS FROM A NITRATION PROCESS

(71) Applicants: NORAM International Limited, Dublin (IE); Steven D. Buchi, Vancouver (CA); Alfred A. Guenkel, Vancouver (CA)

(72) Inventors: Steven D. Buchi, Vancouver (CA); Alfred A. Guenkel, Vancouver (CA)

(73) Assignee: NORAM INTERNATIONAL LIMITED, Dublin (IE)

(*) Notice: Subject to any disclaimer, the term of this patent is extended or adjusted under 35 U.S.C. 154(b) by 0 days.

(21) Appl. No.: 15/735,014

(22) PCT Filed: Jun. 12, 2015

(86) PCT No.: PCT/IB2015/054482
§ 371 (c)(1),
(2) Date: Dec. 8, 2017

(87) PCT Pub. No.: WO2016/198921
PCT Pub. Date: Dec. 15, 2016

(65) Prior Publication Data
US 2018/0155269 A1   Jun. 7, 2018

(51) Int. Cl.
| | |
|---|---|
| C07C 201/16 | (2006.01) |
| C07C 205/06 | (2006.01) |
| C01C 1/10 | (2006.01) |
| C07C 205/17 | (2006.01) |
| C02F 1/20 | (2006.01) |
| C02F 3/02 | (2006.01) |

(Continued)

(52) U.S. Cl.
CPC .............. *C07C 201/16* (2013.01); *C01C 1/10* (2013.01); *C02F 1/20* (2013.01); *C07C 205/06* (2013.01); *C07C 205/17* (2013.01); *C02F 3/02* (2013.01); *C02F 2101/345* (2013.01); *C02F 2101/38* (2013.01); *C02F 2103/36* (2013.01); *Y02W 10/15* (2015.05)

(58) Field of Classification Search
CPC ........................... C07C 201/16; C07C 205/06
See application file for complete search history.

(56) References Cited

U.S. PATENT DOCUMENTS

| | | |
|---|---|---|
| 4,230,567 A | 10/1980 | Larbig |
| 4,597,567 A | 7/1986 | Racca |

(Continued)

FOREIGN PATENT DOCUMENTS

| | | |
|---|---|---|
| CA | 2835121 C | 11/2012 |
| HU | P0100200 A1 | 5/2001 |

(Continued)

*Primary Examiner* — Jafar F Parsa
(74) *Attorney, Agent, or Firm* — Kirton McConkie; Evan R. Witt

(57) ABSTRACT

A process for removing impurities from crude nitrated aromatic products obtained during the nitration of aromatic compounds. The nitrated aromatic products are purified by treatment with ammonia washing followed by caustic washing. The nitrophenolic-containing wash waters are treated to recover dissolved organics and ammonia, and the stripped ammonia-wash effluent is incinerated. Carbon dioxide, which can accumulate in the process, is purged to the caustic washer.

28 Claims, 2 Drawing Sheets

US 10,155,719 B2

Page 2

(51) Int. Cl.
*C02F 1/34* (2006.01)
*C02F 101/34* (2006.01)
*C02F 101/38* (2006.01)
*C02F 103/36* (2006.01)

(56) References Cited

U.S. PATENT DOCUMENTS

| | | |
|---|---|---|
| 4,604,214 A | 8/1986 | Carr et al. |
| 4,925,565 A | 5/1990 | Adams et al. |
| 5,250,193 A | 10/1993 | Sawicki et al. |
| 6,288,289 B1 | 9/2001 | Boyd et al. |
| 6,506,948 B1 | 1/2003 | Sawicki |
| 8,801,932 B2 | 8/2014 | Gattrell |
| 2007/0088183 A1 | 4/2007 | Hermann et al. |
| 2013/0041189 A1* | 2/2013 | Deckert ............... C07C 201/16 568/939 |

FOREIGN PATENT DOCUMENTS

| | | |
|---|---|---|
| HU | 226079 B1 | 4/2008 |
| WO | 2012/156095 A1 | 11/2012 |
| WO | 2012156095 A1 | 11/2012 |
| WO | 2013/020798 A1 | 2/2013 |
| WO | 2013020798 A1 | 2/2013 |

* cited by examiner

METHOD OF PURIFYING NITRATED AROMATIC COMPOUNDS FROM A NITRATION PROCESS

FIELD OF THE INVENTION

The invention pertains to the purification of nitrated aromatic products by removing nitro-phenolics and other oxidation by-products.

BACKGROUND OF THE INVENTION

In nitration processes to produce nitrated aromatic products, nitro-phenolic species and other oxidative decomposition compounds are formed as by-products. For example, nitration of benzene produces nitrophenols, nitration of toluene produces nitrocresols, and nitration of xylene produces nitroxylenols. The crude nitrated aromatic product requires purification to remove these by-products before it is suitable as a feedstock to downstream hydrogenation processes, where these impurities are believed to adversely affect the catalyst performance.

The purification of nitrated aromatic products is commonly practiced industrially by contacting the crude nitrated organic with an alkaline water stream in a multi-stage counter-current washing system. The nitro-phenolics and other oxidation compounds, which are organic acids, are neutralized into their respective organic salt form and extracted into the alkaline water phase to produce a water effluent stream rich in nitro-phenolics and other oxidation species. This process is well known, and is described in the patent literature: U.S. Pat. No. 6,288,289 (Boyd et al.); U.S. Pat. No. 4,604,214 (Carr et al.); U.S. Pat. No. 6,506,948 (Sawicki); US 2007/0088183 (Hermann et al.); and WO 2012/156095 (Polmann et al.).

The generated effluent stream is commonly known as strong effluent or red water, due to its high nitro-phenolic concentration and its strong characteristic color. The treatment of this effluent stream is particularly challenging since some nitro-phenolics are highly bio-toxic, such that biological wastewater treatment plants can only tolerate very low concentrations. Therefore, this effluent stream usually requires pre-treatment to reduce its toxicity before it can be discharged to a biological treatment facility.

There are several effluent treatment technologies currently in use to treat this strong effluent stream. These include: thermal destruction (U.S. Pat. No. 4,230,567), wet oxidation (U.S. Pat. No. 5,250,193, U.S. Pat. No. 8,801, 932), solvent extraction (U.S. Pat. No. 4,597,567 and U.S. Pat. No. 4,925,565), ozonation (U.S. Pat. No. 4,604,214) and incineration/thermal oxidation (U.S. Pat. No. 6,288, 289). The optimum treatment technology is dependent on many factors, including local site conditions, economics and operator preference. In addition, the selected treatment technology is dependent on the type of base used to provide alkalinity in the nitrated product purification system.

In most industrial plants, caustic soda (sodium hydroxide) is used as the washing base to provide the required alkalinity for the nitrated product purification process; however, aqueous ammonia is used in a small fraction of industrial nitration processes. The reason for caustic soda being favored is that it is a stronger base than ammonia, and as such, results in superior washing efficiency and leads to higher product quality, with lower nitro-phenolic and oxidation species in the final washed nitrated aromatic product. Ammonia, being a weaker base, is not able to effectively neutralize and thereby extract some of the weaker organic acid by-products (i.e., those which have higher pKa values). In addition, caustic is non-volatile whereas ammonia exerts a significant vapor pressure and may deposit unstable ammonium nitrite salts formed by reacting ammonia with NOx present in the nitration plant vent.

However, ammonia may be the preferred washing base if incineration/thermal oxidation is chosen as the strong effluent treatment option. In general, inorganic salts produce ash in the incinerator which can attack the refractory lining and require the installation of a slag collection system; whereas, ammonia is reduced to nitrogen in a thermal oxidizer so there are no ash deposits to deal with.

Operating costs of incineration can be fairly high due to the large amount of water that has to be vaporized. However, in some circumstances incineration may be an attractive option as it has the benefit of not requiring further treatment, such as a biological treatment, and can reduce total capital investment costs of a project. It can also achieve competitive operating costs where there is a low cost of energy or alternatively where the effluent stream can be used to offset water already used in an incineration process.

In summary, selecting caustic soda as the washing base results in improved product quality but requires additional treatment processes to treat the generated strong effluent. Alternatively, selecting ammonia allows for incineration/thermal oxidation which can eliminate the requirement for further treatment processes but results in reduced product quality, which may negatively affect the downstream processes.

SUMMARY OF THE INVENTION

This invention incorporates both ammonia and caustic soda (or another suitable strong base) as the washing bases to purify the nitrated aromatic product; whereas the prior art teaches to use either ammonia or caustic depending on the selected manner in which the strong effluent is to be treated. The crude nitrated aromatic product, for example nitrobenzene, nitrotoluene or nitroxylene, is first washed with an aqueous ammonia solution, by which a portion of the nitro-phenolics and other oxidation by-products are extracted, producing a strong effluent stream suitable for treatment by incineration/thermal oxidation. Subsequently, the ammonia-washed nitrated aromatic product is washed with a caustic solution to extract the remaining by-products and achieve a high product quality of the washed nitrated aromatic compound. The caustic effluent generated in the caustic washing step has surprisingly been found to be of a quality, due to its low level of bio-toxicity, such that it can be fed directly to a biological treatment system without the requirement for additional treatment technologies.

Additional unit operations may also be incorporated into the method of the invention to reduce overall chemical consumption and improve operating costs, such as effluent stripping/distillation or effluent concentration. The effluent may be stripped to recover ammonia and organic product which is then recycled back to the washing step. The ammonia strong effluent stream may be concentrated by evaporation to reduce the water load on the downstream effluent treatment process.

According to one embodiment, the invention provides a method of purifying a nitroaromatic product containing nitro-hydroxy-aromatic by-products produced in a nitration process, comprising the steps of: (a) washing the nitrated aromatic product containing nitro-hydroxy-aromatic by-products with an alkaline aqueous solution comprising ammonia to convert some of the nitro-hydroxy-aromatic by-products into their respective nitro-hydroxy-aromatic ammonium salts; (b) separating an aqueous wash stream containing the nitro-hydroxy-aromatic ammonium salts formed in step (a) from an organic stream comprising ammonia-washed nitroaromatic product; (c) washing the ammonia-washed nitroaromatic product with an aqueous solution comprising a base stronger than ammonia to convert the nitro-hydroxy-aromatic by-products that were not removed in steps (a) and (b) into their respective nitro-hydroxy-aromatic salts; and (d) separating an aqueous wash stream comprising the nitro-hydroxy-aromatic salts produced in step (c) from an organic stream comprising washed nitroaromatic product.

According to some embodiments, the base stronger than ammonia comprises an alkali metal hydroxide, such as caustic soda or potassium hydroxide, or an alkaline earth hydroxide, such as calcium hydroxide.

Further aspects of the invention and features of specific embodiments are described below.

DETAILED DESCRIPTION OF THE INVENTION

Embodiments of the invention are described below in which the selected strong base is caustic soda. However, it will be understood that caustic soda is only one example of a strong base that can be employed. Other bases that are stronger than ammonia may also be used in the invention, examples being other alkali metal hydroxides, including potassium hydroxide, and alkaline earth hydroxides, including calcium hydroxide.

Figure 1:
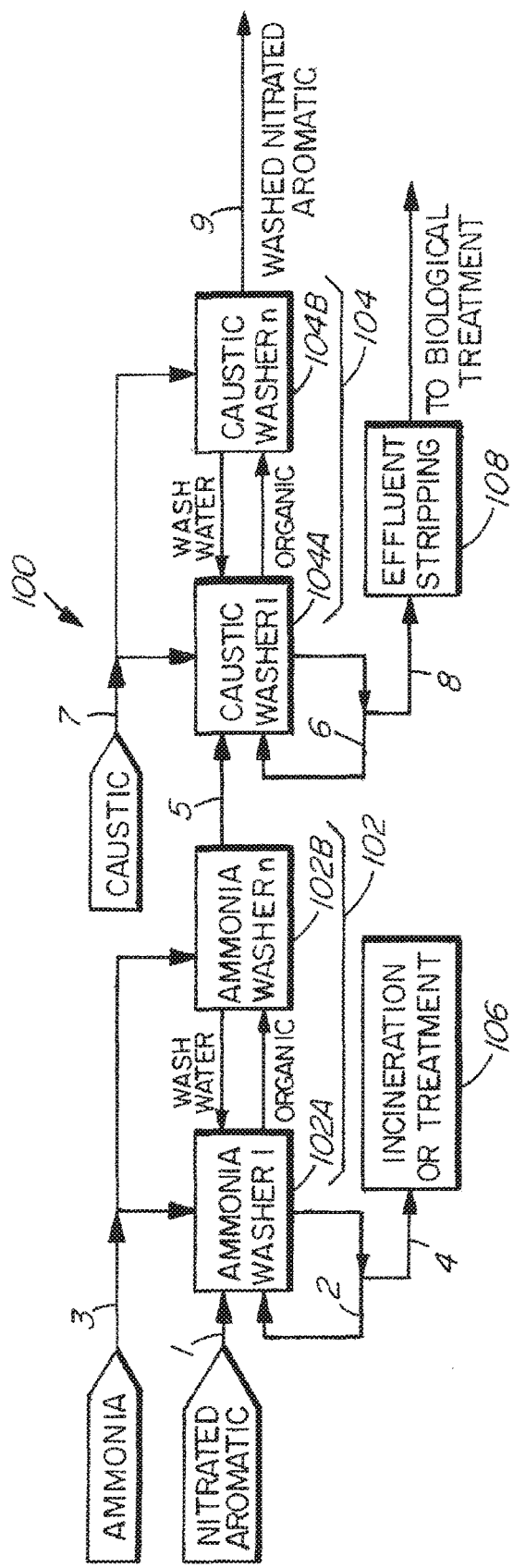
FIG. 1 is a schematic block diagram illustrating one embodiment of the invention for purifying nitrated aromatic products.

Referring first to FIG. 1, a nitrated aromatic purification system 100 has an ammonia washing stage 102 followed by a caustic washing stage 104. The ammonia washing stage and the caustic washing stage both have one or more counter-current washers. For purposes of illustration, FIG. 1 shows two counter-current ammonia washers 102A and 102B and two counter-current caustic washers 104A and 104B; and it will be understood that any number of washers suitable for a particular application may be used. The washing stages 102, 104 may employ either a stirred tank, a washing column, or a static mixer followed by a separator. The purification system has an aqueous stream of ammonia 3 to feed into the ammonia washers, and an aqueous stream of caustic soda 7 to feed into the caustic washers. Fresh water or process water can be used in both washing stages 102, 104. The purification system includes a recirculating aqueous ammonia wash stream 2 to feed into the first ammonia washer 102A and an aqueous caustic wash stream 6 to feed into the first caustic washer 104A.

In the purification process, a stream of the crude nitrated aromatic product 1, such as mononitrobenzene, from a nitration process is first contacted with the aqueous ammonia wash stream 2 in the ammonia washing stage 102. Here, mineral acids and the stronger (i.e., lower pKa) organic acids are converted to their respective ammonium salt form and extracted from the nitrated aromatic product into the aqueous wash phase (stream 2). The ammonia 3 provides the necessary alkalinity for this conversion. A portion of the aqueous ammonia wash stream 2, now containing impurities as organic salts, becomes the strong effluent stream 4 and is conveyed directly to incineration/thermal oxidation 106, or to an alternative treatment process.

The ammonia-washed nitrated aromatic product stream 5, which still contains a portion of the weaker nitrophenolic organic acids, leaves the ammonia wash stage and is contacted with the aqueous caustic wash stream 6 in the caustic wash stage 104. Here, the remaining nitrophenolic organic acids are converted to their respective sodium organic salt form by the caustic soda and extracted from the nitrated organic into the aqueous caustic wash phase (stream 6). A portion of the aqueous caustic wash stream 6, now containing the remainder of the organic salt impurities, becomes the caustic effluent stream 8. This stream 8 may be sent to an effluent stripping column 108, where dissolved nitrated aromatics are recovered via either direct or indirect steam stripping. As it contains only a small portion of the nitrophenolic species and is below bio-toxicity limits after combining with other water streams produced in the process, the caustic effluent stream 8 can then be conveyed directly to biological treatment without the requirement for additional treatment.

The final washed nitrated aromatic stream 9 is essentially free of all mineral acids as well as nitrophenolics and other acidic oxidative species. This stream may then be sent to a stripping or distillation process for further purification. It may also be further water-washed to reduce the salt content in the final washed nitrated aromatic product prior to stripping or distillation.

Figure 2:
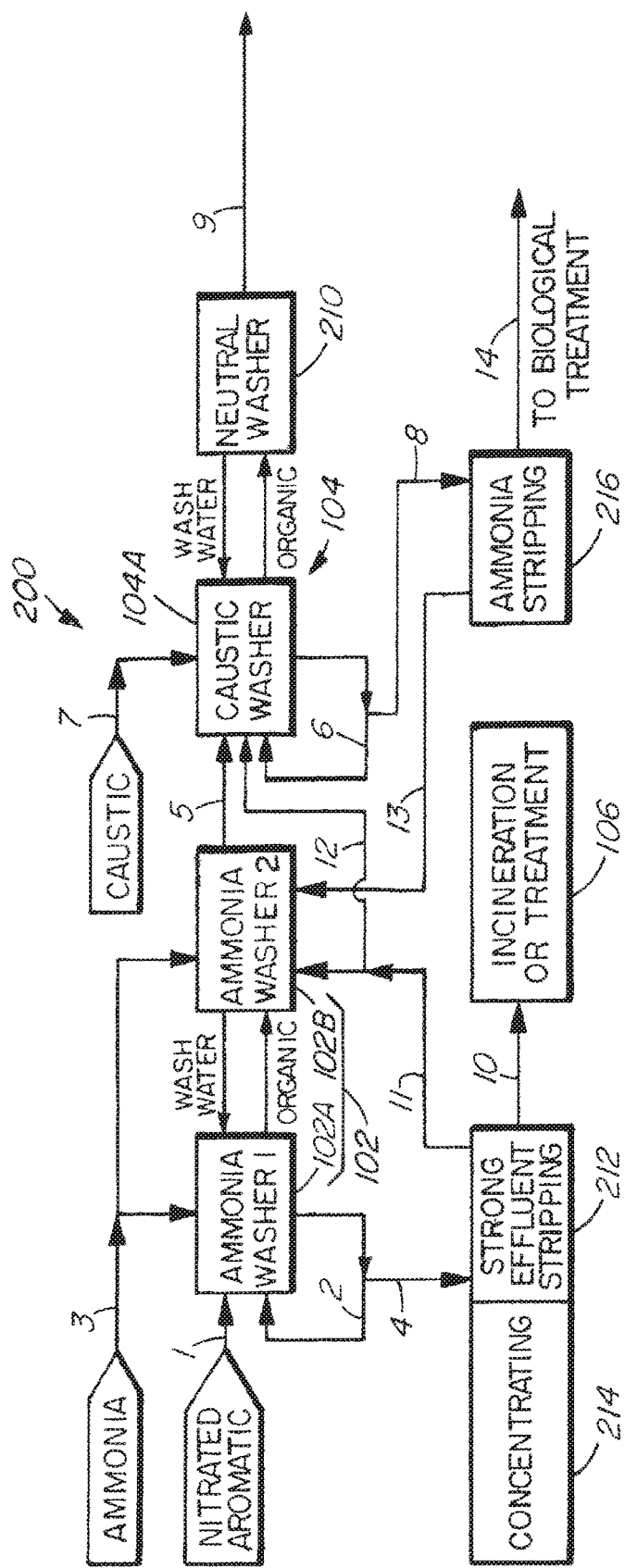
FIG. 2 is a schematic block diagram illustrating a second embodiment of the invention which includes stripping of the ammonia effluent and the caustic effluent.

Referring next to FIG. 2, which illustrates a second purification system 200, the purification is achieved in essentially the same way as described above and includes some additional steps. Corresponding steps and parts are indicated by the same reference characters used in FIG. 1. The purification system 200 includes stripping of the ammonia effluent 4 and the caustic effluent 8, and the addition of a neutral water wash stage 210 downstream of the caustic wash stage 104.

In the purification system 200, the strong effluent stream 4 from the ammonia wash is first sent to a strong effluent stripper 212 to recover dissolved nitrated aromatics and excess washing base prior to the stripped effluent 10 being sent to incineration/thermal oxidation 106 or to an alternative treatment process. This stripping of the strong effluent is accomplished via either direct or indirect steam stripping. The overhead condensate stream 11 from the stripper 212, containing the recovered nitrated aromatics as well as excess ammonia, is returned to the ammonia washing stage 102. Surprisingly, with a strong effluent stripper, a sub-stoichiometric consumption of ammonia was found to be required to neutralize and extract the nitrophenolics and other acidic oxidative species. Without precluding other possible explanations, it is believed that this result is possible due to an equilibrium shift as the ammonia is stripped, which results in some of the organic salts reverting back to their acidic form while still remaining dissolved in the strong effluent. This sub-stoichiometric consumption of washing base has the benefit of lowering the net consumption of chemicals.

Optionally, the strong effluent stream 4 is sent to a concentration unit 214 either as an alternative or in combination with stripper 212. The concentration unit may use low grade energy to boil off water, thereby reducing the amount of water to be vaporized in the incinerator/thermal oxidizer. The boiled-off water can be condensed and returned to washing with the condensate stream 11.

We discovered that the strong effluent stripper 212 or concentrator 214 requires a condensate purge stream 12 to be implemented. Unexpectedly, we found that carbon dioxide and other components, which are formed as part of the nitration process, will become trapped in the ammonia washing stage 102. For the case of carbon dioxide, the mechanism is thought to be that carbon dioxide entering the ammonia washing stage 102 is converted to ammonium carbonate ($(NH_4)_2CO_3$), which is then sent to the strong effluent stripper 212, where it decomposes back to ammonia and carbon dioxide and is returned back to the ammonia washing stage 102, thereby building up. This causes operational problems, as the carbonate will exceed solubility and begin to precipitate and plug the equipment and piping. Our solution was to purge a portion of the condensate (purge stream 12), which would contain the highest concentration of carbon dioxide, to the caustic washing system 104. By doing this, the carbon dioxide is captured and converted to sodium carbonate ($Na_2CO_3$), which is a non-volatile and stable form that will be eventually be purged from the system via the caustic effluent stream 8.

This caustic effluent stream 8 is sent to an ammonia stripper 216, where dissolved nitrated aromatics and ammonia which entered the caustic washing stage either by water entrainment in the ammonia-washed organic stream 5 or by ammonia in the purge stream 12 are recovered via either direct or indirect steam stripping. The overhead condensate stream 13 from the ammonia stripper 216, containing the recovered nitrated aromatics and ammonia, is returned to the ammonia washing stage 102. The carbon dioxide in carbonate form remains in the stripped caustic effluent 14, which can now be conveyed to biological treatment. The ammonia stripper 216 may or may not be required depending on the economics of recovered chemicals and/or maximum ammonia nitrogen limits acceptable to the biological treatment plant.

The purification method of the invention can be used to purify many nitroaromatic products, including nitrobenzenes, nitrotoluenes and nitroxylenes, removing by-products comprising nitrophenols, nitrocresols and nitroxylenols, respectively.

Example 1

The washing process of the invention was carried out on a laboratory scale. The composition for the crude mononitrobenzene (MNB) (equivalent to stream 1 in the description above) used in the experiment was analyzed to be:
Mono-nitrophenols: 362 ppmw
Di-nitrophenols: 1,122 ppmw
Picric acid: 97 ppmw
The remainder was MNB, with some excess benzene from the nitration reaction, dissolved water and other minor impurities.

Following an ammonia washing stage, analysis of the ammonia-washed MNB (equivalent to stream 5) yielded the following composition:
Mono-nitrophenols: 213 ppmw
Di-nitrophenols: <5 ppmw
Picric acid: 13 ppmw
The remainder was MNB, with some excess benzene from the nitration reaction, dissolved water and other minor impurities.

These results show that the ammonia washing stage was able to remove essentially all of the di-nitrophenols which make up the majority of the impurities in the nitrobenzene; however, a significant portion of the mono-nitrophenols remained, as they have a relatively higher pKa than the other forms. Some picric acid also remained in the ammonia washed MNB; this was surprising, as it was believed that it would be more easily removed due to its low pKa value.

Upon subsequent Caustic Washing of the ammonia-washed MNB, analysis showed that the remainder of the nitrophenols were removed from the caustic washed MNB (equivalent to stream 9).

This caustic-washed MNB stream can then be sent to stripping or distillation to remove the benzene, DNB and other non-acid impurities.

Example 2

The following stream table presents the operating data for an industrial mononitrobenzene purification process, which was modelled after the embodiment of FIG. 2. The stream numbers set forth in Table 1 correspond to the stream numbers of FIG. 2.

TABLE 1

|  |  | Stream No. | | | | | | |
| --- | --- | --- | --- | --- | --- | --- | --- | --- |
|  |  | 1 | 2 | 3 | 4 | 5 | 6 | 7 |
| Total Flow | kg/h | 35,962.5 | 54,000.0 | 78.0 | 5,193.0 | 36,072.7 | 54,000.0 | 45.3 |
| Temperature | °C. | 55 | 68 | 17 | 65 | 61 | 60 | 54 |
| Nitrobenzene | 1 | 33,550.7 | 166.1 | 0.0 | 16.0 | 33,556.9 | 412.4 | 0.0 |
| Benzene | 2 | 1,921.6 | 0.0 | 0.0 | 0.0 | 1,950.1 | 14.4 | 0.0 |
| Nitrophenols | 3 | 63.3 | 0.0 | 0.0 | 0.0 | 5.0 | 0.0 | 0.0 |
| Other Organic Impurities | 4 | 167.7 | 0.0 | 0.0 | 0.0 | 169.1 | 1.2 | 0.0 |
| Sulfuric Acid | 5 | 1.4 | 2.2 | 0.0 | 0.2 | 0.0 | 0.0 | 0.0 |
| Water | 6 | 249.1 | 52,604.8 | 71.7 | 5,058.9 | 382.8 | 51,929.6 | 38.5 |
| Ammonia | 7 | 0.0 | 499.8 | 6.2 | 48.1 | 1.9 | 1,240.3 | 0.0 |
| Ammonium Nitrophenolates | 8 | 0.0 | 660.8 | 0.0 | 63.6 | 0.1 | 2.2 | 0.0 |
| Ammonium Sulphate | 9 | 0.0 | 20.9 | 0.0 | 2.0 | 0.0 | 0.1 | 0.0 |
| Ammonium Carbonate | 10 | 0.0 | 45.4 | 0.0 | 4.4 | 0.0 | 0.0 | 0.0 |
| Sodium Hydroxide | 11 | 0.0 | 0.0 | 0.0 | 0.0 | 0.0 | 134.2 | 6.8 |
| Sodium Nitrophenolates | 12 | 0.0 | 0.0 | 0.0 | 0.0 | 0.0 | 145.0 | 0.0 |

TABLE 1-continued

| | | Stream No. | | | | | | |
|---|---|---|---|---|---|---|---|---|
| | | 1 | 2 | 3 | 4 | 5 | 6 | 7 |
| Sodium Carbonate | 13 | 0.0 | 0.0 | 0.0 | 0.0 | 0.0 | 120.6 | 0.0 |
| Dissolved Gases (CO$_2$/NO$x$) | 14 | 8.7 | 0.0 | 0.0 | 0.0 | 6.8 | 0.0 | 0.0 |

| | | Stream No. | | | | | | |
|---|---|---|---|---|---|---|---|---|
| | | 8 | 9 | 10 | 11 | 12 | 13 | 14 |
| Total Flow | kg/h | 2,156.4 | 39,552.8 | 5,439.7 | 687.4 | 687.4 | 370.3 | 2,237.8 |
| Temperature | °C. | 60 | 61 | 50 | 45 | 45 | 45 | 35 |
| Nitrobenzene | 1 | 16.5 | 37,026.3 | 0.1 | 15.9 | 15.9 | 16.4 | 0.0 |
| Benzene | 2 | 0.6 | 2,020.0 | 0.0 | 0.0 | 0.0 | 0.6 | 0.0 |
| Nitrophenols | 3 | 0.0 | 0.0 | 0.0 | 0.0 | 0.0 | 0.0 | 0.0 |
| Other Organic Impurities | 4 | 0.0 | 170.8 | 0.0 | 0.0 | 0.0 | 0.0 | 0.0 |
| Sulfuric Acid | 5 | 0.0 | 0.0 | 0.2 | 0.0 | 0.0 | 0.0 | 0.0 |
| Water | 6 | 2,073.7 | 328.9 | 5,373.6 | 619.3 | 619.3 | 303.9 | 2,221.6 |
| Ammonia | 7 | 49.5 | 0.2 | 0.3 | 47.8 | 47.8 | 49.4 | 0.1 |
| Ammonium Nitrophenolates | 8 | 0.1 | 0.0 | 63.6 | 0.0 | 0.0 | 0.0 | 0.1 |
| Ammonium Sulphate | 9 | 0.0 | 0.0 | 2.0 | 0.0 | 0.0 | 0.0 | 0.0 |
| Ammonium Carbonate | 10 | 0.0 | 0.0 | 0.0 | 4.4 | 4.4 | 0.0 | 0.0 |
| Sodium Hydroxide | 11 | 5.4 | 0.0 | 0.0 | 0.0 | 0.0 | 0.0 | 5.4 |
| Sodium Nitrophenolates | 12 | 5.8 | 0.0 | 0.0 | 0.0 | 0.0 | 0.0 | 5.8 |
| Sodium Carbonate | 13 | 4.8 | 0.0 | 0.0 | 0.0 | 0.0 | 0.0 | 4.8 |
| Dissolved Gases (CO$_2$/NO$x$) | 14 | 0.0 | 6.7 | 0.0 | 0.0 | 0.0 | 0.0 | 0.0 |

In this example, the strong effluent stream 10 was sent to a coal gasification process, where this effluent stream was used to off-set water used in creating the slurry sent to gasification. This allowed the strong effluent stream to be thermally oxidized for essentially zero energy cost as the water was already required to create the slurry.

The caustic effluent stream 14 was diluted, with the nitration reaction water generated in the process, by approximately 10:1 before being sent outside battery limits and directly to biological treatment.

Throughout the foregoing description and the drawings, specific details have been set forth in order to provide a more thorough understanding to persons skilled in the art. However, well known elements may not have been shown or described in detail to avoid unnecessarily obscuring the disclosure. For example, various conduits and pumps which provide means to convey streams of reactants and products, and some unit operations commonly used in nitration purification processes, may not have been shown. Accordingly, the description and drawings are to be regarded in an illustrative, rather than a restrictive, sense.

As will be apparent to those skilled in the art in the light of the foregoing disclosure, many alterations and modifications are possible in the practice of this invention without departing from the scope thereof. Accordingly, the scope of the invention is to be construed in accordance with the following claims.

The invention claimed is:

1. A method of purifying a nitroaromatic product containing nitro-hydroxy-aromatic by-products produced in a nitration process, comprising the steps of:
   (a) washing the nitrated aromatic product containing nitro-hydroxy-aromatic by-products with an alkaline aqueous solution comprising ammonia to convert some of the nitro-hydroxy-aromatic by-products into their respective nitro-hydroxy-aromatic ammonium salts;
   (b) separating an aqueous wash stream containing the nitro-hydroxy-aromatic ammonium salts formed in step (a) from an organic stream comprising ammonia-washed nitroaromatic product;
   (c) washing the ammonia-washed nitroaromatic product with an aqueous alkali metal hydroxide solution to convert the nitro-hydroxy-aromatic by-products that were not removed in steps (a) and (b) into their respective nitro-hydroxy-aromatic alkali-metal salts; and
   (d) separating an aqueous wash stream comprising the nitro-hydroxy-aromatic alkali-metal salts produced in step (c) from an organic stream comprising alkali-metal-hydroxide-washed nitroaromatic product.

2. The method according to claim 1, further comprising the step of stripping or concentrating the aqueous wash stream of step (b) to produce a condensate stream comprising nitroaromatic product and ammonia and a stripped effluent stream.

3. The method according to claim 2, further comprising the step of recycling the condensate stream to the ammonia washing of step (a).

4. The method according to claim 2, further comprising the step of treating the stripped effluent stream by incineration or thermal oxidation.

5. The method according to claim 3, further comprising purging a portion of the condensate stream to the caustic washing of step (c).

6. The method according to claim 1, further comprising the step of stripping at least a portion of the aqueous wash stream of step (d) to produce a condensate stream comprising recovered nitroaromatic product and ammonia and a stripped caustic effluent stream.

7. The method according to claim 6, further comprising the step of conveying the condensate stream comprising recovered nitroaromatic product and ammonia to the ammonia washing of step (a).

8. The method according to claim 6, further comprising the step of biological treatment of the stripped caustic effluent stream.

9. The method according to claim 1, wherein the nitroaromatic product comprises mononitrobenzene and the nitro-hydroxy-aromatic by-products comprise nitrophenols.

10. The method according to claim 1, wherein the nitroaromatic product comprises nitrotoluenes and the nitro-hydroxy-aromatic by-products comprise nitrocresols.

11. The method according to claim 1, wherein the nitroaromatic product comprises nitroxylenes and the nitro-hydroxy-aromatic by-products comprise nitroxylenols.

12. The method according to claim 1, further comprising the step of treating the aqueous wash stream containing nitrophenolic ammonium salts by incineration or thermal oxidation.

13. The method according to claim 1, wherein the alkali metal hydroxide is sodium hydroxide.

14. The method according to claim 1, wherein the alkali metal hydroxide is potassium hydroxide.

15. A method of purifying a nitroaromatic product containing nitro-hydroxy-aromatic by-products produced in a nitration process, comprising the steps of:
  (a) washing the nitrated aromatic product containing nitro-hydroxy-aromatic by-products with an alkaline aqueous solution comprising ammonia to convert some of the nitro-hydroxy-aromatic by-products into their respective nitro-hydroxy-aromatic ammonium salts;
  (b) separating an aqueous wash stream containing the nitro-hydroxy-aromatic ammonium salts formed in step (a) from an organic stream comprising ammonia-washed nitroaromatic product;
  (c) washing the ammonia-washed nitroaromatic product with an aqueous solution comprising a base stronger than ammonia to convert the nitro-hydroxy-aromatic by-products that were not removed in steps (a) and (b) into their respective nitro-hydroxy-aromatic salts; and
  (d) separating an aqueous wash stream comprising the nitro-hydroxy-aromatic salts produced in step (c) from an organic stream comprising washed nitroaromatic product.

16. The method according to claim 15, wherein the base stronger than ammonia comprises an alkaline earth hydroxide.

17. The method according to claim 16, wherein the alkaline earth hydroxide comprises calcium hydroxide.

18. The method according to claim 15, further comprising the step of stripping or concentrating the aqueous wash stream of step (b) to produce a condensate stream comprising nitroaromatic product and ammonia and a stripped effluent stream.

19. The method according to claim 18, further comprising the step of recycling the condensate stream to the ammonia washing of step (a).

20. The method according to claim 18, further comprising the step of treating the stripped effluent stream by incineration or thermal oxidation.

21. The method according to claim 20, further comprising purging a portion of the condensate stream to the caustic washing of step (c).

22. The method according to claim 15, further comprising the step of stripping at least a portion of the aqueous wash stream of step (d) to produce a condensate stream comprising recovered nitroaromatic product and ammonia and a stripped caustic effluent stream.

23. The method according to claim 22, further comprising the step of conveying the condensate stream comprising recovered nitroaromatic product and ammonia to the ammonia washing of step (a).

24. The method according to claim 22, further comprising the step of biological treatment of the stripped caustic effluent stream.

25. The method according to claim 15, wherein the nitroaromatic product comprises mononitrobenzene and the nitro-hydroxy-aromatic by-products comprise nitrophenols.

26. The method according to claim 15, wherein the nitroaromatic product comprises nitrotoluenes and the nitro-hydroxy-aromatic by-products comprise nitrocresols.

27. The method according to claim 15, wherein the nitroaromatic product comprises nitroxylenes and the nitro-hydroxy-aromatic by-products comprise nitroxylenols.

28. The method according to claim 15, further comprising the step of treating the aqueous wash stream containing nitrophenolic ammonium salts by incineration or thermal oxidation.

* * * * *